United States Patent
Guha et al.

(10) Patent No.: US 11,406,599 B2
(45) Date of Patent: Aug. 9, 2022

(54) PELLET AND MULTI-UNIT PELLET SYSTEM (MUPS)

(71) Applicant: Evonik Operations GmbH, Essen (DE)

(72) Inventors: Ashish Guha, Mumbai (IN); Shraddha Joshi, Thane (IN); Aditi Poddar, Navi Mumbai (IN); Suresh Doke, Maharashtra (IN)

(73) Assignee: Evonik Operations GmbH, Essen (DE)

( * ) Notice: Subject to any disclaimer, the term of this patent is extended or adjusted under 35 U.S.C. 154(b) by 0 days.

(21) Appl. No.: 17/606,928

(22) PCT Filed: Mar. 26, 2020

(86) PCT No.: PCT/EP2020/058534
§ 371 (c)(1),
(2) Date: Oct. 27, 2021

(87) PCT Pub. No.: WO2020/221522
PCT Pub. Date: Nov. 5, 2020

(65) Prior Publication Data
US 2022/0142928 A1    May 12, 2022

(30) Foreign Application Priority Data
Apr. 30, 2019 (IN) .............. 201941017213

(51) Int. Cl.
*A61K 9/20* (2006.01)
(52) U.S. Cl.
CPC .......... *A61K 9/2081* (2013.01); *A61K 9/2027* (2013.01); *A61K 9/2095* (2013.01)
(58) Field of Classification Search
None
See application file for complete search history.

(56) References Cited

U.S. PATENT DOCUMENTS

| 9,668,977 B2 | 6/2017 | Schattka et al. |
| 9,844,511 B2 | 12/2017 | Nollenberger et al. |
| 2011/0150945 A1 * | 6/2011 | Spitz ............ A61K 9/5078 514/338 |
| 2014/0079792 A1 | 3/2014 | Schattka et al. |
| 2014/0086997 A1 | 3/2014 | Nollenberger et al. |

FOREIGN PATENT DOCUMENTS

| EP | 2720681 | 11/2016 |
| EP | 2720682 | 11/2016 |
| WO | 2012/171575 | 12/2012 |
| WO | WO-2014032741 A1 * | 3/2014 ........ A61K 31/135 |

OTHER PUBLICATIONS

U.S. Pat. No. 9,668,977, Jun. 6, 2017, 2014/0079792, Schattka et al.
U.S. Pat. No. 9,844,511, Dec. 19, 2017, 2014/0086997, Nollenberger et al.
Anonymous, "*Evonik Launches EUDRAGIT FL 30 D-55*", XP055622506, Oct. 4, 2018, pp. 1-2.
European Search Report dated Feb. 12, 2020 in European Application No. 19195080.7, 7 pages.
International Search Report dated Jul. 23, 2020 in PCT/EP2020/058534, 5 pages.
"*Waiver of In Vivo Bioavailability and Bioequivalence Studies for Immediate-Release Solid Oral Dosage Forms Based on a Biopharmaceutics Classification System Guidance for Industry*", U.S. Department of Health and Human Services Food and Drug Administration Center for Drug Evaluation and Research (CDER), Biopharmaceutics, Dec. 2017, pp. 1-16.
Written Opinion dated Jul. 23, 2020 in PCT/EP2020/058534, 6 pages.

* cited by examiner

*Primary Examiner* — Lakshmi S Channavajjala
(74) *Attorney, Agent, or Firm* — Grüneberg and Myers PLLC

(57) ABSTRACT

A pellet contains a core, which contains one or more biologically active ingredients, and a coating layer on the core. The coating layer contains a mixture of a first polymer and a second polymer. The first polymer is a core-shell polymer, containing 50 to 90% by weight of a core, containing polymerized units of 60 to 85% by weight of ethyl acrylate and 20 to 40% by weight of methyl methacrylate; and 10 to 50% by weight of a shell, containing polymerized units of 40 to 60% by weight ethyl acrylate and 40 to 60% by weight methacrylic acid. The second polymer contains polymerized units of 40 to 60% by weight of methacrylic acid and 60 to 40% by weight of ethyl acrylate or methyl methacrylate. A Multi-Unit Pellet System (MUPS), preferably a compressed tablet, contains a multitude of the pellets.

11 Claims, No Drawings

PELLET AND MULTI-UNIT PELLET SYSTEM (MUPS)

CROSS-REFERENCE TO RELATED APPLICATIONS

This application is the National Stage entry under § 371 of International Application No. PCT/EP2020/058534, filed on Mar. 26, 2020, and which claims the benefit of priority to Indian Application No. 201941017213, filed on Apr. 30, 2019. The content of each of these applications is hereby incorporated by reference in entirety.

BACKGROUND OF THE INVENTION

Field of the Invention

The invention is in the field of pellets and Multi-Unit Pellet Systems (MUPS), preferably compressed tablets, comprising a multitude of such pellets.

Description of Related Art Background

WO2012/171575A1 describes a coating composition suitable for pharmaceutical applications. The coating composition comprises core-shell polymers derived from two-stage emulsion polymerization processes.

EUDRAGIT® FL 30 D-55 (Evonik Nutrition & Care GmbH, Darmstadt, Germany) is a commercially available 30% by weight aqueous dispersion of a copolymer from a two-stage emulsion polymerization process, with a core of about 75% by weight, comprising polymerized units of 70% by weight of ethyl acrylate and 30% by weight of methyl methacrylate, and a shell of about 25% by weight, comprising polymerized units of 50% by weight ethyl acrylate and 50% by weight methacrylic acid.

SUMMARY OF THE INVENTION

When formulating Multi-Unit Pellet System (MUPS), especially MUPS tablets, the most frequent problem encountered is pellets film coat cracking and/or alteration of release profiles. Physical combination of anionic acrylates (example EUDRAGIT® L 30 D-55) with neutral acrylates (example EUDRAGIT® NM 30 D-55) has been described previously in order to take care of flexibility and release characteristics, but this approach suffers from multiple limitations like; 1. Need of additional cumbersome step of neutralization before mixing of two polymers. 2. Significant slowing down of release profiles after compression when high quantities of neutral acrylate polymer is used. 3. Cracking of films after compression, when low quantities of neutral acrylate polymer are used leading to loss of enteric protection. Thus, there is a need to improve the coating composition and process for enteric coating of Multi-Unit Pellet System (MUPS) dosage forms intended to be compressed into tablets.

The invention is concerned with a pellet comprising a core, comprising one or more biologically active ingredients, and a coating layer onto the core, wherein the coating layer is comprising a mixture of a first polymer, which is a core-shell polymer, comprising 50 to 90, preferably 70 to 80% by weight of a core, comprising polymerized units of 60 to 80, preferably 65 to 75% by weight of ethyl acrylate and 20 to 40, preferably 25 to 35% by weight of methyl methacrylate, and 10 to 50, preferably 20 to 30% by weight of a shell, comprising polymerized units of 40 to 60, preferably 45 to 55% by weight of ethyl acrylate and 40 to 60, preferably 45 to 55% by weight of methacrylic acid, and a second polymer, comprising polymerized units of 40 to 60% by weight of methacrylic acid and 60 to 40% by weight of ethyl acrylate or methyl methacrylate, wherein the ratio of the first polymer to the second polymer is from about 1:0.1 to 1:10, preferably from 1:0.1 to 1:2.5, most preferred from 1:0.25 to 1:2. Also disclosed is a Multi-Unit Pellet System (MUPS), preferably a compressed tablet, comprising a multitude of the pellets.

DETAILED DESCRIPTION OF THE INVENTION

Pellet

The invention discloses a pellet, comprising a coating, which can be used in the form of a multitude of pellets comprised in a Multi-Unit Pellet Systems (MUPS), preferably in a compressed tablet.

The term Multi-Unit Pellet Systems (MUPS) is well known to a person skilled in the art of pharmacy, galenics or nutraceutical technology. A typical example for a Multi-Unit Pellet Systems (MUPS) is a compressed tablet comprising a multitude of pellets, comprising a core, comprising one or more biologically active ingredients, and a coating layer onto the core. The coated pellets are after compression bound in a matrix of pharmaceutically or nutraceutically excipients, such as microcrystalline cellulose or lactose. During the compression step of such tablets the pellets undergo high mechanical stress. Therefore, there is a need for flexible coatings that are on one hand resistant to the compression step and on the other hand provide certain active ingredient release profiles as required for the certain therapeutic purpose.

The invention discloses a pellet comprising a core, comprising one or more biologically active ingredients, and a coating layer onto the core, wherein the coating layer is comprising a mixture of a first polymer, which is a core-shell polymer, comprising 50 to 90, preferably 70 to 80% by weight of a core, comprising polymerized units of 60 to 80, preferably 65 to 75% by weight of ethyl acrylate and 20 to 40, preferably 25 to 35% by weight of methyl methacrylate, and 10 to 50, preferably 20 to 30% by weight of a shell, comprising polymerized units of 40 to 60, preferably 45 to 55% by weight of ethyl acrylate and 40 to 60. preferably 45 to 55% by weight of methacrylic acid, and a second polymer, comprising polymerized units of 40 to 60% by weight of methacrylic acid and 60 to 40% by weight of ethyl acrylate or methyl methacrylate, wherein the ratio of the first polymer to the second polymer is from about 1:0.1 to 1:10, preferably from 1:0.1 to 1:2.5, most preferred from 1:0.25 to 1:2.

A preferred pellet is comprising a core, comprising one or more biologically active ingredients, and a coating layer onto the core, wherein the coating layer is comprising a mixture of a first polymer, which is a core-shell polymer, comprising 70 to 80% by weight of a core, comprising polymerized units of 65 to 75% by weight of ethyl acrylate and 25 to 35% by weight of methyl methacrylate, and 20 to 30% by weight of a shell, comprising polymerized units of 45 to 55% by weight of ethyl acrylate and 45 to 55% by weight of methacrylic acid, and a second polymer, comprising polymerized units of 40 to 60% by weight of methacrylic acid and 60 to 40% by weight of ethyl acrylate or methyl methacrylate, wherein the ratio of the first polymer to the second polymer is from 1:0.1 to 1:2.5, most preferred from 1:0.25 to 1:2.

The core and/or the coating layer of the pellet may further comprise pharmaceutical or nutraceutical acceptable excipients.

The pellet may comprise 40 to 90% by weight of the core and 10 to 60% by weight of the coating layer.

Core

The pellet comprises a core, comprising one or more biologically active ingredients.

The core of the pellet may further comprise pharmaceutical or nutraceutical acceptable excipients or substrate pellets (nonpareilles, for instance sugar pellets).

The core may comprise 1 to 100, preferably 10 to 50% by weight of the one or more biologically active ingredients and 0 to 99, preferably 50 to 90% by weight of pharmaceutical or nutraceutical acceptable excipients and/or substrate pellets (non pareilles)

Separating Layer

The core of the pellet may optionally comprise, as a part of the core, an additional separating layer as an outer layer, for instance a layer of a water-soluble polymer, such as hydroxypropyl methyl cellulose. The separating layer may have the function to separate the active ingredient in the core from the acidic groups of the coating layer and has essentially no influence on the active ingredient release. The amount of the separating layer may be from 5 to 60, preferably from 10 to 30% by weight related to the weight of the total core.

Coating Layer

The pellet comprises a coating layer onto the core, respectively on the separating layer of the core, wherein the coating layer is comprising a mixture of a first polymer and a second polymer, wherein the ratio of the first polymer to the second polymer is from about 1:0.1 to 1:10, preferably from 1:0.1 to 1:2.5, most preferred from 1:0.25 to 1:2.

The coating layer of the pellet may further comprise pharmaceutical or nutraceutical acceptable excipients, such as talc, $TiO_2$, stearates or pigments.

First Polymer

The coating layer comprises a first polymer which is a core-shell polymer, comprising 50 to 90, preferably 70 to 80% by weight of a core, comprising polymerized units of 60 to 80, preferably 65 to 75% by weight of ethyl acrylate and 20 to 40, preferably 25 to 35% by weight of methyl methacrylate, and 10 to 50, preferably 20 to 30% by weight of a shell, comprising polymerized units of 40 to 60, preferably 45 to 55% by weight of ethyl acrylate and 40 to 60, preferably 45 to 55% by weight of methacrylic acid.

A suitable first polymer is EUDRAGIT® FL 30 D-55 (Evonik Nutrition & Care GmbH, Darmstadt, Germany), which is a commercially available 30% by weight aqueous dispersion of a copolymer from a two-stage emulsion polymerization process, with a core of about 75% by weight, comprising polymerized units of 70% by weight of ethyl acrylate and 30% by weight of methyl methacrylate, and a shell of about 25% by weight, comprising polymerized units of 50% by weight ethyl acrylate and 50% by weight methacrylic acid.

Second Polymer

The coating layer comprises a second polymer, comprising polymerized units of 40 to 60% by weight of methacrylic acid and 60 to 40% by weight of ethyl acrylate or methyl methacrylate. The second polymer is not a core-shell polymer.

The coating layer may comprise a second polymer comprising polymerized units of 40 to 60% by weight of methacrylic acid and 60 to 40% by weight of methyl methacrylate (type EUDRAGIT® L).

Preferably the coating layer comprises a second polymer comprising polymerized units of 40 to 60% by weight of methacrylic acid and 60 to 40% by weight of ethyl acrylate (type EUDRAGIT® L 100-55).

A suitable second polymer is EUDRAGIT® L 100-55 Evonik Nutrition & Care GmbH, Darmstadt, Germany), which is a copolymer comprising polymerized units of 50% by weight of methacrylic acid and 50% by weight of ethyl acrylate. EUDRAGIT® L 30 D-55 is a 30% by weight aqueous dispersion of EUDRAGIT® L 100-55.

Ratio of the Amount of Polymer in the Core of the First Polymer to the Amount of Polymer in the Shell of the First Polymer and the Second Polymer A preferred ratio of the amount of polymer by weight in the core of the first polymer to the amount of polymer in the shell of the first polymer and the second polymer may be in the range of 5:95 to 70:30, preferably in the range of 20:80 to 60:40 (in the examples referred to as "Ratio of NM:L in coating").

Plasticizers

It is an advantage that the combination of the first and the second polymer in the coating layer of the pellet does not need any essential addition or no addition at all of a plasticizer. This facilitates the composition, the processing and reduces the risk of incompatibilities or undesired side-effects, that may be potentially caused in some cases by the addition of plasticizers.

The coating layer may comprise no essential amounts, 2% by weight or less (0 to 2% by weight) of a plasticizer or does not comprise a plasticizer at all.

Plasticizers may be defined in that they achieve through physical interaction with a polymer a reduction in the glass transition temperature and promote film formation, depending on the added amount. Suitable substances usually have a molecular weight of between 100 and 20,000 and comprise one or more hydrophilic groups in the molecule, e.g. hydroxyl, ester or amino groups.

The coating layer may comprise no essential amounts of a plasticizer, preferably 2% by weight or less (0 to 2% by weight) of a plasticizer, which is selected from the groups of alkyl citrates, glycerol esters, alkyl phthalates, alkyl sebacates, sucrose esters, sorbitan esters and polyethylene glycols. The coating layer may preferably comprise no plasticizer at all.

The coating layer may comprise no essential amounts of a plasticizer, preferably 2% by weight or less (0 to 2% by weight) of a plasticizer, which is selected from triethyl citrate (TEC), acetyl triethyl citrate (ATEC), diethyl sebacate and dibutyl sebacate (DBS), glycerol, propylene glycol, polyethylene glycols 200 to 12,000 and castor oil. The coating layer may preferably comprise no plasticizer at all.

Biologically Active Ingredient

The pellet comprises one or more biologically active ingredients that may be selected from active pharmaceutical ingredients and active nutraceutical ingredients.

The one or more biologically active ingredient may be selected from the groups of analgetics, antibiotics or anti-infectives, antibodies, antiepileptics, antigens from plants, antirheumatics, betablocker, benzimidazole derivatives, beta-blocker, cardiovascular drugs, chemotherapeutics, CNS drugs, digitalis glycosides, gastrointestinal drugs, e.g. proton pump inhibitors, combinations of proton pump inhibitors with a nonsteroidal anti-inflammatory drug (NSAID), enzymes, hormons, liquid or solid natural extracts, oligonucleotides, peptidhormon proteins, therapeutical bacteria, peptides, proteins, urology drugs and vaccines, including salt-forms, such as aspartates or hydrochlorides.

Preferably, the one or more biologically active ingredients may be selected from gastrointestinal drugs, preferably from proton pump inhibitors, most preferably from esomeprazole, dexlansoprazole, lansoprazole, omeprazole, pantoprazole and rabeprazole or any combinations thereof, and a combination of esomeprazole and naproxen.

Preferably, the one or more biologically active ingredients may be selected from a combination of a proton pump inhibitor and a further active pharmaceutical ingredient. An example for such a combination may be esomeprazole and naproxen (known from Vimovo™, AstraZeneca AB, Sweden).

Multi-Unit Pellet System (MUPS)

The term Multi-Unit Pellet Systems (MUPS) is well known to a person skilled in the art of pharmacy, galenics or nutraceutical technology.

The term "a multitude of pellets" shall be understood in that for instance about 10 to 100,000, preferably about 20 to 10,000, more preferably 50 to 2,000 pellets may be comprised per single dosage unit of the Multi-Unit Pellet System (MUPS), which may be a single capsule, a single sachet or a single tablet.

The Multi-Unit Pellet System (MUPS) is comprising a multitude of the pellets as disclosed.

The Multi-Unit Pellet System (MUPS), wherein the multitude of pellets is comprised may be a capsule, in a sachet or in a tablet.

The average particle size d50 of the pellets may be in the range of 1 to 2000, preferably in the range of 10 to 1000, most preferably in the range of 100 to 600 μm. The average diameter may be determined by sieving or by laser diffraction according to the United States Pharmacopeia 36 (USP) chapter <429> and European Pharmacopeia 7.0 (EP) chapter 2.9.31. The laser diffraction method is based on the phenomenon that particles scatter light in all directions with an intensity pattern that is dependent on particle size. A representative sample, dispersed at an adequate concentration in a suitable liquid or gas, is passed through the beam of a monochromic light source usually from a laser. The light scattered by the particles at various angles is measured by a multi-element detector, and numerical values relating to the scattering pattern are then recorded for subsequent analysis. The numerical scattering values are then transformed, using an appropriate optical model and mathematical procedure, to yield the proportion of total volume to a discrete number of size classes forming a volumetric particle size distribution (d50 describes a particle diameter corresponding to 50% of cumulative undersize distribution).

Capsule

When the Multi-Unit Pellet System (MUPS) is a capsule, preferably a hard-shell capsule, the capsule is comprising a multitude of pellets.

Such a capsule dosage form may be of specific advantage since it is not necessary to add effective amounts of plasticizers to the pellet coating. This facilitates the composition, the processing and reduces the risk of incompatibilities or unwanted side effects, that may be caused by the addition of plasticizers.

Sachet

A sachet may have the form of a sealed packet containing a multitude of pellets embedded in pharmaceutical or nutraceutical excipients.

When the Multi-Unit Pellet System (MUPS) is a sachet, the sachet is comprising a multitude of pellets.

Such a sachet dosage form may be of specific advantage since it is not necessary to add effective amounts of plasticizers to the pellet coating. This facilitates the composition, the processing and reduces the risk of incompatibilities or undesired side effects, that may be potentially caused in some cases by the addition of plasticizers.

Compressed Tablet

When the Multi-Unit Pellet System (MUPS) is a tablet, the tablet may be a compressed tablet, comprising the multitude of pellets embedded in matrix excipients.

The compressed tablet may comprise 30 to 80, preferably 40 to 70% by weight of matrix excipients and 70 to 20, preferably 60 to 30% by weight pellets.

Matrix excipients may be selected from the group of antioxidants, brighteners, binding agents, cushioning agents, flavoring agents, flow aids, glidants, penetration-promoting agents, pigments, plasticizers, polymers, pore-forming agents and stabilizers or any combinations thereof.

Preferably the matrix excipients may comprise microcrystalline cellulose, glycerol monostearate, lactose, silica, croscarmellose sodium and/or sodium stearyl fumarate.

The compressed tablet may comprise 20 to 60% by weight of pellets and 40 to 80% by weight of matrix excipients.

The weight of the compressed tablet may be from 50 to 2000 mg, preferably 100 to 1000 mg and most preferably from 200 to 800 mg.

The forces applied in the compression process may be in the range of 1 bis 10 kN, preferably 2-6 kN. The resulting tablet hardness may be in the range of 50 to 250, preferably 80 to 150 N. Methods and equipment for determining the hardness of a tablet are well known to a skilled person in the field of pharmacy, galenics or nutraceutical technology.

The compressed tablet as disclosed may be characterized in that the release of the biologically active ingredient from the compressed tablets (including the pellets in their matrix) is higher than that of the pellets. Usually such a release profile is acceptable and no calculation of a similarity factor F2 is necessary.

The compressed tablet as disclosed may be further characterized in that the release curves of the biologically active ingredient from the compressed tablets (including the pellets in their matrix) is faster in a pH 4.5 medium or higher in a pH 6.8 medium (according to USP) than that of the pellets. Usually such a release profile is acceptable and no calculation of a similarity factor F2 is necessary.

The compressed tablet as disclosed may also be characterized in that the release curves, respectively the dissolution profiles of the biologically active ingredient from the pellets and that of the compressed tablets (including the pellets in their matrix) show a similarity factor, F2-value, of 50 or more. Two dissolution profiles are considered similar when the f2 value is ≥50. Thus, these release profiles are also acceptable.

F2-Value

The F2-value is known to the skilled person from the requirements for bioequivalence studies as defined by Food and Drug Administration (FDA) of the United States of America. These are for example available in the documents like "Guidance for Industry; Waiver if In Vivo Bioavailability and Bioequivalence Studies for Immediate-Release Solid Oral Dosage Forms Based on Biopharmaceutics Classification System (U.S. Department of Health and Human Services, Food and Drug Administration, Center for Drug Evaluation and Research (CDER), August 2000) or other from versions of this document, or from other document or guidelines from the FDA or CDER concerning bioavailability and bioequivalence Studies. All these documents are available in the Internet and well known to the skilled person in the field of pharmacy and galenics. In the above-mentioned document from August 2000 the calculation of the similarity factor (f2) is defined on p. 7:

When comparing the test and reference products, dissolution profiles should be compared using a similarity factor (f2). The similarity factor is a logarithmic reciprocal square root transformation of the sum of squared error and is a measurement of the similarity in the percent (%) of dissolution between the two curves.

$$f2=50 \cdot \log\{[1+(1/n)\Sigma t=1 n(Rt-Tt)2]-0.5 \cdot 100\}$$

Two dissolution profiles are considered similar when the f2 value is
Release Rates The release rates of the one or more biologically active ingredient(s) from the pellets and that of the compressed tablets should be preferably 10% or less after 1 hour in 0.1 HCl and more than 50% in subsequent pH 6.8 buffer (phosphate-buffer according to USP (e.g. USP-42-NF-37, March 2019) after 2 hours at pH 6.8. The determination of the release rates according to USP is well known to a skilled person (USP-42-NF-37, March 2019, Apparatus USP type II (Paddle), 75 RPM).
Process Disclosed is a process for preparing a Multi-Unit Pellet System (MUPS) which is a compressed tablet by providing pellets comprising a core, comprising a biologically active ingredient, and a coating layer, comprising a mixture of a first polymer, with is a core-shell polymer, comprising 50 to 90, preferably 70 to 80% by weight of a core, comprising polymerized units of 60 to 80, preferably 65 to 75% by weight of ethyl acrylate and 20 to 40, preferably 25 to 35% by weight of methyl methacrylate, and 10 to 50, preferably 20 to 30% by weight of a shell, comprising polymerized units of 40 to 60, preferably 45 to 55% by weight of ethyl acrylate and 40 to 60, preferably 45 to 55% by weight of methacrylic acid, and a second polymer, polymerized from 40 to 60% by weight of methacrylic acid and 40 to 60% by weight of ethyl acrylate or methyl methacrylate, wherein the ratio of the first polymer to the second polymer is from about 1:0.1 to 1:10, preferably from 1:0.1 to 1:2.5, adding matrix excipients and compression of the mixture to a compressed tablet.
Medical Use Disclosed is a Multi-Unit Pellet System (MUPS) as described herein, comprising a biologically active ingredient, preferably a compressed tablet, for use as a medicament in the therapy and treatment of a disease of the human or animal body, wherein the disease is selected from ulcers of the stomach and duodenum, NSAID-induced ulcers, *Helicobacter pylori* infections, gastrointestinal reflux disease or Zollinger-Ellison syndrome, arthrosis, pain and inflammation and wherein the biologically active ingredient is selected from esomeprazole, dexlansoprazole, lansoprazole, omeprazole, pantoprazole and rabeprazole or any combinations thereof and from a combination of esomeprazole and naproxen.

Disclosed is a Multi-Unit Pellet System (MUPS) as described herein, comprising a biologically active ingredient, preferably a compressed tablet, for use (method of treatment) as a medicament in the therapy and treatment of a disease of the human or animal body, wherein the disease is selected from ulcers of the stomach and duodenum, NSAID-induced ulcers, *Helicobacter pylori* infections, gastrointestinal reflux disease or Zollinger-Ellison syndrome, arthrosis, pain and inflammation and wherein the biologically active ingredient is selected from a combination of a proton pump inhibitor with a nonsteroidal anti-inflammatory drug (NSAID), preferably a combination of esomeprazole and naproxen.

TABLE 2

Formula for MUPS (C1-C6)

| Ingredients | % |
|---|---|
| Coated pellers | 42.81 |
| MCC 101 granules (#20 passed) | 10.81 |
| MCC 102 | 3 |
| MCC 200 | 29.53 |
| Ceolus KG 802 | 10.31 |
| Ac Di sol SD 711 | 2.26 |
| Aerosil 200 | 0.71 |
| Sodium Stearyl fumarate | 0.57 |
| Total | 100.00 |

Abbreviations:
HPMC: Hydroxy propyl cellulose,
cps: centipoise,
TiO$_2$: Titanium dioxide,
MCC: Microcrystalline cellulose

TABLE 1

Formula (C1-C6) Formula for coating of pellets

| Ingredients | C1 | C2 | C3 | C4 | C5 | C6 |
|---|---|---|---|---|---|---|
| | % w/w composition | | | | | |
| Lansoprazole | 8.87 | 7.04 | 7.84 | 7.03 | 7.84 | 6.81 |
| Substrate pellets | 62.11 | 49.26 | 54.89 | 49.19 | 54.87 | 47.69 |
| HPMC (3 cps) | 10.65 | 8.44 | 9.41 | 8.43 | 9.41 | 8.18 |
| TiO$_2$ | 2.13 | 1.69 | 1.88 | 1.69 | 1.88 | 1.64 |
| Eudragit ® NM 30 D | — | — | 7.68 | 10.33 | 10.75 | 14.02 |
| Eudragit ® L 30 D-55 | — | — | 7.68 | 10.33 | 10.75 | 14.02 |
| Eudragit ® FL 30 D-55 | 8.70 | 20.69 | — | — | — | — |
| Sodium hydroxide | — | — | 0.10 | 0.14 | 0.14 | 0.19 |
| Talc | 7.54 | 12.88 | 10.50 | 12.86 | 10.50 | 13.47 |
| Total | 100.00 | 100.00 | 100.00 | 100.00 | 100.00 | 100.00 |

Process Details for Experiment C1-C7
(1) Preparation of coating solution for pellets coating: C1
  I. To a part of water, talc was added and homogenized for 15-20 min.
  II. Remaining part of water was used to rinse the homogenizer and added to Step I.
  III. Dispersion of Step II added to EUDRAGIT® FL 30 D-55 under stirring.
  IV. Stirring was continued till 10 min.
  V. The coating dispersion was passed through 40 #ASTM sieve (425 μm)
(2) Preparation of coating solution for pellets coating: C2-C7
  I. To a part of water talc was homogenized for about for 15-20 min.
  II. Remaining part of water was used to rinse the homogenizer and added to Step I.
  III. Dispersion of Step II was added to EUDRAGIT® NM 30 D under stirring.
  IV. EUDRAGIT® L 30 D-55 was neutralized (by 6%) using 1N NaOH. The pH was brought to around 5.
  V. The dispersion of Step IV was added to Step III, slowly under stirring.

VI. The final coating solution was passed through 40 #ASTM sieve (425 μm)

(3) Coating of pellets

The commercially procured Lansoprazole pellets (18 #-20 #) were barrier coated with HPMC and then was coated with functional coat (Please refer the Formula section) The general process parameters are enlisted below:

TABLE 3

Process details

| (4) Experiment number Parameters | Unit | C1*-C2 Value | C3-C6 Value |
|---|---|---|---|
| Equipment setup | | | |
| Nozzle bore | mm | 0.8 | 0.8 |
| Internal silicone tube diameter | mm | 2 | 2.5 |
| Process parameter setup | | | |
| Atomizing air pressure | bar | 1.0 | 1.0 |
| Filter shaking Interval | sec | Manual | 180 |
| Filter shaking | sec | — | 05 |
| Air flow | m³/h | 12.0-18.0 | 30-60 |
| Process data | | | |
| Inlet Temperature | ° C. | 31-35 | 32-35 |
| Product Temperature | ° C. | 26-30 | 27-36 |
| Spray rate | g/min | — | 2-6 |

*Batch was executed in Huttlin Microlab (small batch size)

(4) Process for tablets/MUPS compression

I. The coated pellets were mixed with tableting excipients.

II. The compression was carried out using D tooling fitted on a rotary compression machine.

(5) Process for tablets/MUPS compression

III. The coated pellets were mixed with tableting excipients.

IV. The compression was carried out using D tooling fitted on a rotary compression machine.

TABLE 4

Set tablet compression parameters

| | Experiment number | | | | | |
|---|---|---|---|---|---|---|
| | C1 | C2 | C3 | C4 | C5 | C6 |
| Punch size (mm) | 10.00 | 11.00 | 11.00 | 11.00 | 11.00 | 11.00 |
| Set Weight (mg) | 395 | 498 | 448 | 500 | 448 | 498 |
| Observed Hardness (N) | 110-130 | 110-130 | 100-110 | 100-100 | 100-100 | 100-110 |

TABLE 5

Comparative examples C1 to C4:
Performance of EUDRAGIT ® FL 30 D-55 and physical mixtures of EUDRAGIT ® L 30 D-55 with EUDRAGIT ® NM 30 D (50:50)

| | | C1 | | C2 | | C3 | | C4 | |
|---|---|---|---|---|---|---|---|---|---|
| | | Lansoprazole barrier coated pellets. Functional coating with EUDRAGIT ® FL 30 D-55 | | | | Lansoprazole pellets barrier coated with HPMC and further with a functional coating layer of polymeric mixture of EUDRAGIT ® NM 30D and EUDRAGIT ® L 30 D-55. Pellets further compressed into tablets along with excipients | | | |
| Examples | | Pellets | Tablets | Pellets | Tablets | Pellets | Tablets | Pellets | Tablets |
| Ratio of NM:L in coating | | 75:25 | — | 75:25 | — | 50:50 | — | 50:50 | — |
| Process without additional neutralization step | | Yes | — | Yes | — | No | — | No | — |
| Polymeric coat build up (% w/w) w.r.t core | | 10 | — | 30 | — | 20 | — | 30 | — |
| Enteric protextion (<10% release in 0.1N HCl, 1 hr) | | Yes | Yes | Yes | Yes | Yes | Yes | Yes | Yes |
| % Drug release within 2 hrs of pH 6.8 buffer exposure more than 50% | | No | No | No | No | Yes | Yes | Yes | Yes |
| Drug release in 0.1N HCl followed by pH 6.8 | 1 hr** | 0.44* | 3.10** | 1.30** | 3.32** | 0.00** | 2.97** | 3.78** | 2.98** |
| | 0.5 hr | 30.00 | 27.18 | 21.83 | 10.35 | 84.29 | 66.85 | 46.98 | 46.17 |
| | 1 hr | 34.80 | 32.53 | 24.60 | 14.44 | 103.00 | 89.33 | 101.00 | 80.67 |
| | 1.5 hr | 38.26 | 39.57 | — | — | 104.00 | 93.46 | 103.00 | 84.79 |
| | 2 hr | — | — | — | — | — | — | — | — |
| F2 value* comparing dissolution profiles of pellets and compressed tablets (≥50% denotes similarity) | | 81 | | 52 | | 45 | | 43 | |

TABLE 5-continued

Comparative examples C1 to C4:
Performance of EUDRAGIT ® FL 30 D-55 and physical mixtures of EUDRAGIT ® L 30 D-55 with EUDRAGIT ® NM 30 D (50:50)

|  | C1 | | C2 | | C3 | | C4 | |
|---|---|---|---|---|---|---|---|---|
|  | Lansoprazole barrier coated pellets. Functional coating with EUDRAGIT ® FL 30 D-55 | | | | Lansoprazole pellets barrier coated with HPMC and further with a functional coating layer of polymeric mixture of EUDRAGIT ® NM 30D and EUDRAGIT ® L 30 D-55. Pellets further compressed into tablets along with excipients | | | |
| Examples | Pellets | Tablets | Pellets | Tablets | Pellets | Tablets | Pellets | Tablets |
| Comments | Not acceptable. Slow release from pellets and tablets | | Not acceptable. Slow release from pellets and tablets | | Not acceptable. Pellets and tablet profiles significantly dissimilar, Additional neutralization step needed. | | Not acceptable. Pellets and tablet profiles significantly dissimilar, Additional neutralization step needed. | |

*No F2 verification needed if the release in tablets is faster than pellets in buffer phase **Release in 0.1N HCl

TABLE 6

Comparative examples C5 and C6: Performance of physical mixture of EUDRAGIT ® L 30 D-55 with EUDRAGIT ® NM 30 D (30:70)

|  | C5 | | C6 | |
|---|---|---|---|---|
| Examples | Lansoprazole pellets barrier coated with HPMC and further with a functional coating layer of polymeric mixture of EUDRAGIT ® NM 30D and EUDRAGIT ® L 30 D-55. Pellets further compressed into tablets along with excipients | | | |
| Formulation details | Pellets | Tablets | Pellets | Tablets |
| Ratio of NM:L in coating | 30:70 | — | 30:70 | — |
| Process without additional neutralization step | No | — | No | — |
| Polymeric coat build up (% w/w) w.r.t core | 20 | — | 30 | — |
| Enteric protection (<10% release in 0.1N HCl, 1 hr) | Yes | No | Yes | Yes |
| % Drug release within 2 hrs of pH 6.8 buffer exposure more than 50% | Yes | Yes | Yes | Yes |
| Drug release in 0.1N HCl followed by pH 6.8    1 hr** | 0.05** | 9.74** | 0.35** | 8.73** |
| 0.5 hr | 77.32 | 54.10 | 26.68 | 26.34 |
| 1 hr | 100.00 | 70.80 | 92.93 | 61.65 |
| 1.5 hr | 103.00 | 77.74 | 99.99 | 70.81 |
| 2 hr | — | — | — | — |
| F2 value* comparing dissolution profiles of pellets and compressed tablets (50% denotes similarity) | 32 | | 33 | |
| Comments | Not acceptable. Pellets and tablet dissolution profiles significantly dissimilar, Additional neutralization step needed. | | Not acceptable. Pellets and tablet dissolution profiles significantly dissimilar. Additional neutralization step needed. | |

*No F2 verification needed if the release in tablets is faster than pellets in buffer phase; **Release in 0.1N HCl.

TABLE 7

Formula for coating of pellets

|  | Experiment number | | | | | | | | |
|---|---|---|---|---|---|---|---|---|---|
| Ingredients | I1 | I2 | I3 | I4 | I5 | I6 | I7 | I8 | I9 |
|  | % w/w composition | | | | | | | | |
| Lansoprazole | 8.33 | 7.63 | 7.04 | 7.42 | 7.04 | 6.56 | 6.56 | 4.80 | 5.43 |
| Substrate pellets | 58.31 | 53.40 | 49.26 | 51.95 | 49.26 | 45.93 | 45.93 | 33.61 | 37.98 |
| HPMC (3 cps) | 10.00 | 9.16 | 8.44 | 8.91 | 8.44 | 7.87 | 7.87 | 5.76 | 6.51 |

TABLE 7-continued

Formula for coating of pellets

| Ingredients | Experiment number |  |  |  |  |  |  |  |  |
|---|---|---|---|---|---|---|---|---|---|
|  | I1 | I2 | I3 | I4 | I5 | I6 | I7 | I8 | I9 |
|  | % w/w composition |  |  |  |  |  |  |  |  |
| Eudragit FL ® 30 D-55 | 8.16 | 11.21 | 13.79 | 7.27 | 8.28 | 9.52 | 6.35 | 9.41 | 3.26 |
| Eudragit L ® 30 D-55 | 4.08 | 5.61 | 6.90 | 10.91 | 12.41 | 14.28 | 17.45 | 25.88 | 27.76 |
| Talc | 11.12 | 12.99 | 14.56 | 13.54 | 14.56 | 15.84 | 15.84 | 20.53 | 15.61 |
| Total | 100.00 | 100.00 | 100.00 | 100.00 | 100.00 | 100.00 | 100.00 | 100.00 | 100.00 |

TABLE 8

Formula for MUPS (I1-I9)

| Ingredients | % |
|---|---|
| Coated pellets | 42.81 |
| MCC 101 granules (#20 passed) | 10.81 |
| MCC 102 | 3 |
| MCC 200 | 29.53 |
| Ceolus KG 802 | 10.31 |
| Ac Di sol SD 711 | 2.26 |
| Aerosil 200 | 0.71 |
| Sodium Stearyl fumarate | 0.57 |
| Total | 100.00 |

Abbreviations:
HPMC: Hydroxy propyl cellulose,
cps: centipoise,
MCC: Microcrystalline cellulose Process Details for Experiment I1-I9

(1) Preparation of coating solution for pellets coating: I1-I9
 I. To a part of water talc was homogenized for about for 15-20 min.
 II. Remaining part of water was used to rinse the homogenizer and added to Step I.
 III. Dispersion of EUDRAGIT® FL 30 D-55 was added to EUDRAGIT® L 30 D-55, slowly under stirring.
 IV. The dispersion of Step III was added to Step IV, under stirring.
 V. The final coating solution was passed through 40 #ASTM sieve (425 μm)

(2) Coating of pellets

The commercially procured Lansoprazole pellets (18 #-20 #) were barrier coated with HPMC and then was coated with functional coat (Please refer the Formula section above)

TABLE 9

The general process parameters are enlisted below:
General Process Parameters in GPCG 1.1, bottom spray

| Parameters | Unit | Value |
|---|---|---|
| Equipment setup |  |  |
| Nozzle bore | mm | 0.8 |
| Internal silicone tube diameter | mm | 3 |
| Column Height | mm | 16 |
| Process parameter setup |  |  |
| Atomizing air pressure | bar | 1.0 |
| Filter shaking Interval | sec | 30 |
| Filter shaking | sec | 10 |
| Air flow | m³/h | 60-80 |
| Process data |  |  |
| Inlet Temperature | ° C. | 26-36 |
| Product Temperature | ° C. | 26-27 |
| Spray rate | (g/min) | 2-8 |

(3) Process for tablets/MUPS compression
 I. The coated pellets were mixed with tableting excipients.
 II. The compression was carried out using D tooling fitted on a rotary compression machine.

(4) Set tablet compression parameters

TABLE 10

| | Experiment number | | | | | | | | |
|---|---|---|---|---|---|---|---|---|---|
| | I1 | I2 | I3 | I4 | I5 | I6 | I7 | I8 | I9 |
| Punch size (mm) | 11.00 | 11.00 | 11.00 | 11.0 | 11.00 | 11.0 | 11.0 | 12.5 | 11.00 |
| Set Weight (mg) | 410 | 456 | 495 | 444 | 469 | 504 | 554 | 784 | 565.00 |
| Observed Hardness (N) | 110-120 | 110-120 | 110-120 | 110-120 | 110-120 | 110-120 | 120-130 | 120-130 | 120-130 |

TABLE 11

Inventive examples I1 to I4: Performance of physical mixture of EUDRAGIT ® L 30 D-55 with EUDRAGIT ® FL 30 D-55

Formulation details: Lansoprazole pellets barrier coated with HPMC and further with a functional coating layer of polymeric mixture of EUDRAGIT ® FL 30D-55 and EUDRAGIT ® L 30 D-55. Pellets further compressed into tablets along with excipients

| | I1 | | I2 | | I3 | | I4 | | I5 | | I6 | |
|---|---|---|---|---|---|---|---|---|---|---|---|---|
| | Pellets | Tablets | Pellets | Tablets | Pellets | Tablets | Pellets | Tablets | Pellets | Tablets | Pellets | Tablets |
| Ratio of FL:L polymers used for coating | 1:0.5 | — | 1:0.5 | — | 1:0.5 | — | 1:1.5 | — | 1:1.5 | — | 1:1.5 | — |
| Effective ratio of NM:L | 50:50 | — | 50:50 | — | 50:50 | — | 30:70 | — | 30:70 | — | 30:70 | — |
| Process without additional neutralization step | Yes | — | Yes | — | Yes | — | Yes | — | Yes | — | Yes | — |
| Polymeric coat build up (% w/w) w.r.t core | 15 | — | 22 | — | 30 | — | 25 | — | 30 | — | 37 | — |
| Enteric protection (<10% release in 0.1N HCl, 1 hour) | Yes | Yes | Yes | Yes | Yes | Yes | Yes | Yes | Yes | Yes | Yes | Yes |
| % Drug release in Buffer 6.8 in 2 hrs should be more than 50% | Yes | Yes | Yes | Yes | Yes | Yes | Yes | Yes | Yes | Yes | Yes | Yes |
| Drug release in 0.1N HCl followed by pH 6.8   1 hr** | 0** | 6.13** | 0.55** | 5.03** | 0.52** | 3.77** | 0.21** | 7.38** | 0.36** | 8.71** | 0.11** | 5.03** |
| 0.5 hr | 36.99 | 28.76 | 34.78 | 31.50 | 29.98 | 24.57 | 81.70 | 79.86 | 70.40 | 75.89 | 5.06 | 14.40 |
| 1 hr | 51.30 | 35.75 | 44.49 | 39.00 | 40.89 | 33.08 | 91.10 | 89.30 | 99.70 | 85.29 | 59.60 | 68.10 |
| 1.5 hr | 59.98 | 61.83 | 51.40 | 49.30 | 48.93 | 40.74 | — | 92.75 | 102.00 | 95.10 | 88.12 | 89.70 |
| 2 hr | 68.56 | 81.12 | 60.52 | 55.00 | 56.07 | 52.37 | — | — | 104.00 | 99.45 | — | — |
| F2 value* comparing dissolution profiles of pellets and compressed tablets (≥50% denotes similarity) | 50 | | 67 | | 61 | | 67 | | 53 | | 58 | |
| Comments | Acceptable release profiles. Neutralization of polymers not needed | | Acceptable release profiles. Neutralization of polymers not needed | | Acceptable release profiles. Neutralization of polymers not needed | | Acceptable release profiles. Neutralization of polymers not needed | | Acceptable release profiles. Neutralization of polymers not needed | | Acceptable release profiles. Neutralization of polymers not needed | |

*No F2 verification needed if the release in tablets is faster than pellets in buffer phase; **Release in 0.1N HCl

TABLE 12

Inventive examples I7 to I9: Performance of physical mixture of EUDRAGIT ® FL 30 D-55 with EUDRAGIT ® L 30 D-55

Lansoprazole pellets barrier coated with HPMC and further with a functional coating layer of polymeric mixture of EUDRAGIT ® FL 30D-55 and EUDRAGIT ® L 30 D-55. Pellets further compressed into tablets along with excipients

| | I7 | | I8 | | I9 | |
|---|---|---|---|---|---|---|
| Formulation details | Pellets | Tablets | Pellets | Tablets | Pellets | Tablets |
| Ratio of FL: L polymers used for coating | 1:2.75 | — | 1:2.75 | — | 1:6.75 | — |
| Effective ratio of NM:L | 20:80 | — | 20:80 | — | 10:90 | — |
| Process without additional neutralization step | Yes | | Yes | | Yes | |
| Polymeric Coat build up (% w/w) w.r.t core | 37 | — | 75 | — | 50 | — |

TABLE 12-continued

Inventive examples I7 to I9: Performance of physical mixture of EUDRAGIT ® FL 30 D-55 with EUDRAGIT ® L 30 D-55

| | | Example number | | | | | |
|---|---|---|---|---|---|---|---|
| | | I7 | | I8 | | I9 | |
| | | Lansoprazole pellets barrier coated with HPMC and further with a functional coating layer of polymeric mixture of EUDRAGIT ® FL 30D-55 and EUDRAGIT ® L 30 D-55. Pellets further compressed into tablets along with excipients | | | | | |
| Formulation details | | Pellets | Tablets | Pellets | Tablets | Pellets | Tablets |
| Enteric protection (<10% release in 0.1N HCl, 1 hr) | | Yes | Yes | Yes | Yes | Yes | Yes |
| % Drug release in Buffer 6.8 in 2 hr should be more than 50% | | Yes | Yes | Yes | Yes | Yes | Yes |
| Drug release in | 1 hr** | 0.00** | 5.50** | 0.00** | 1.76** | 0.58** | 8.44** |
| 0.1N HCl | 0.5 hr | 6.12 | 73.40 | 1.60 | 20.00 | 71.97 | 81.50 |
| followed by | 1 hr | 89.70 | 103.00 | 14.80 | 73.80 | 87.20 | 94.68 |
| pH 6.8 | 1.5 hr | 108.00 | 107.00 | 64.50 | 108.00 | 96.18 | 98.03 |
| | 2 hr | 113.00 | 108.00 | 107.00 | 114.00 | 97.11 | 102.39 |
| F2 value* comparing dissolution profiles of pellets and compressed tablets (≥50 % denotes similarity) | | Faster drug release in buffer for tablets compared to coated pellets. No F2 comparison needed | | Faster drug release in buffer for tablets compared to coated pellets. No F2 comparison needed | | Faster drug release in buffer for tablets compared to coated pellets. No F2 comparison needed | |
| Comments | | Acceptable release profiles. Neutralization of polymers not needed. | | Acceptable release profiles. Neutralization of polymers not needed. | | Acceptable release profiles. Neutralization of polymers not needed. | |

*No F2 verification needed if the release in tablets is faster than pellets in buffer phase; **Release in 0.1N HCl

The invention claimed is:

1. A pellet, comprising:
a core, comprising one or more proton pump inhibitors, and
a coating layer onto the core,
wherein the coating layer comprises a mixture of a first polymer and a second polymer,
wherein the first polymer is a core-shell polymer, comprising 50 to 90% by weight of a core-shell polymer core, comprising polymerized units of 60 to 80% by weight of ethyl acrylate and 20 to 40% by weight of methyl methacrylate, and wherein the core-shell polymer comprises 10 to 50% by weight of a core-shell polymer shell, comprising polymerized units of 40 to 60% by weight of ethyl acrylate and 40 to 60% by weight of methacrylic acid,
wherein the second polymer comprises polymerized units of 40 to 60% by weight of methacrylic acid and 60 to 40% by weight of ethyl acrylate or methyl methacrylate,
wherein a ratio of the first polymer to the second polymer is from about 1:0.1 to 1:10, and
wherein the one or more proton pump inhibitors have a release rate from the pellet of 10% or less after 1 hour in 0.1 HCl and more than 50% in subsequent pH 6.8 buffer after 2 hours at pH 6.8.

2. The pellet according to claim 1, wherein the core and/or the coating layer comprise pharmaceutically or nutraceutically acceptable excipients.

3. The pellet according to claim 1, wherein the coating layer comprises 2% by weight or less of a plasticizer.

4. A Multi-Unit Pellet System (MUPS), comprising a multitude of the pellets according to claim 1.

5. The Multi-Unit Pellet System (MUPS) according to claim 4, wherein the MUPS is in the form of a compressed tablet comprising the multitude of pellets embedded in matrix excipients.

6. The Multi-Unit Pellet System (MUPS) according to claim 5, wherein the compressed tablet comprises 30 to 80% by weight of the matrix excipients and 70 to 20% by weight of the pellets.

7. The Multi-Unit Pellet System (MUPS) according to claim 6, wherein the matrix excipients are selected from the group consisting of antioxidants, brighteners, binding agents, cushioning agents, flavoring agents, flow aids, glidants, penetration-promoting agents, pigments, plasticizers, polymers, pore-forming agents, stabilizers, and a combination thereof.

8. The Multi-Unit Pellet System (MUPS) according to claim 5, wherein the matrix excipients comprise microcrystalline cellulose, glycerol monostearate, or lactose.

9. The Multi-Unit Pellet System (MUPS) according to claim 5, wherein a release curve of the one or more proton pump inhibitors from the pellets and that of the compressed tablets show an F2-value of 50 or more.

10. A process for preparing the Multi-Unit Pellet System (MUPS) according to claim 5, the process comprising:
providing the multitude of pellets,
adding the matrix excipients, to obtain a mixture, and
compressing the mixture to a compressed tablet.

11. The pellet according to claim 1, wherein the one or more proton pump inhibitors are selected from the group consisting of esomeprazole, dexlansoprazole, lansoprazole, omeprazole, pantoprazole, rabeprazole, a combination thereof, and a combination of esomeprazole and naproxen.

* * * * *